(12) United States Patent
Scherer

(10) Patent No.: US 7,118,553 B2
(45) Date of Patent: Oct. 10, 2006

(54) AUTO-INJECTOR COMPRISING A RESETTABLE RELEASING SAFETY DEVICE

(75) Inventor: Benjamin Scherer, Uster (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 11/132,715

(22) Filed: May 19, 2005

(65) Prior Publication Data

US 2005/0277885 A1    Dec. 15, 2005

Related U.S. Application Data

(63) Continuation of application No. PCT/CH03/00758, filed on Nov. 17, 2003.

(30) Foreign Application Priority Data

Nov. 25, 2002   (CH) .................................. 1987/02

(51) Int. Cl.
   *A61M 5/20*   (2006.01)
   *A61M 5/32*   (2006.01)
(52) U.S. Cl. ..................... 604/136; 604/196
(58) Field of Classification Search ............ 604/68–72, 604/73, 131, 136, 187, 195, 196, 198, 207
   See application file for complete search history.

(56) References Cited

U.S. PATENT DOCUMENTS 4,722,728 A * 2/1988 Dixon ...................... 604/68
4,874,367 A * 10/1989 Edwards ...................... 604/72
5,399,163 A * 3/1995 Peterson et al. .............. 604/68
5,480,381 A * 1/1996 Weston ........................ 604/68
5,911,703 A * 6/1999 Slate et al. .................... 604/68
6,280,421 B1   8/2001 Kirchhofer et al.
6,669,664 B1 * 12/2003 Slate et al. .................... 604/68
2003/0050592 A1   3/2003 Slate et al.

FOREIGN PATENT DOCUMENTS

EP         1 291 028       * 12/2003
WO    WO 02/47746 A1     6/2002

* cited by examiner

*Primary Examiner*—Sharon Kennedy
(74) *Attorney, Agent, or Firm*—Dorsey & Whitney, LLP

(57) ABSTRACT

An autoinjector including a housing, a receptacle for an active substance, which receptacle, together with a connected injection needle, is displaceable within the housing by spring force for inserting the injection needle into a patient, a piston displaceable within the receptacle by spring force for expelling the active substance, a transfer mechanism for transferring the spring force to the receptacle and/or to the piston, a holding mechanism for holding the transfer mechanism, a releasing mechanism for causing the holding mechanism to release the transfer mechanism when the releasing mechanism is moved from a first position into a second position, and a resetting mechanism for moving the releasing mechanism from the first position into the second position without during the move causing the transfer mechanism to be released.

12 Claims, 2 Drawing Sheets

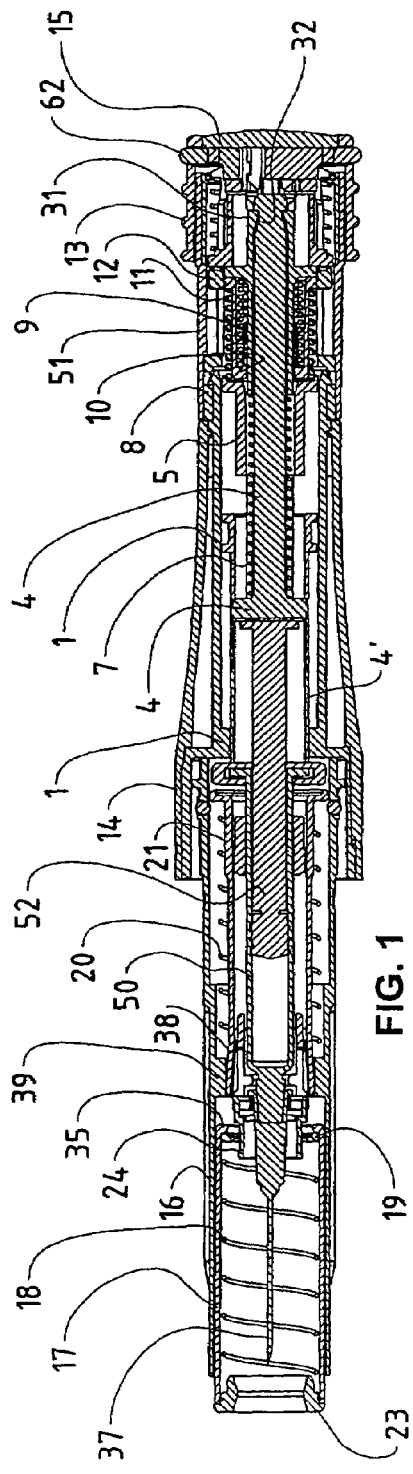
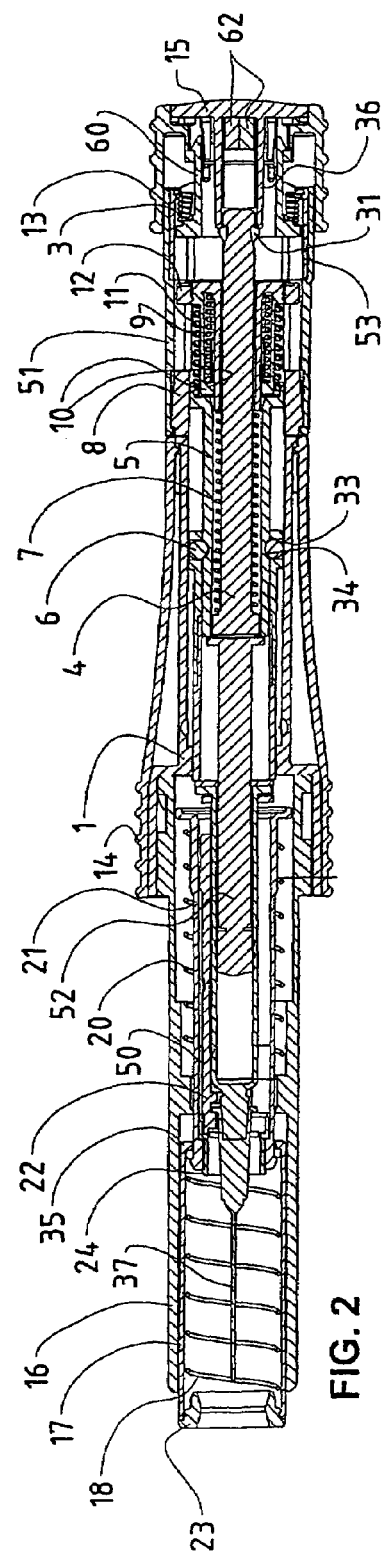
FIG. 1
FIG. 2

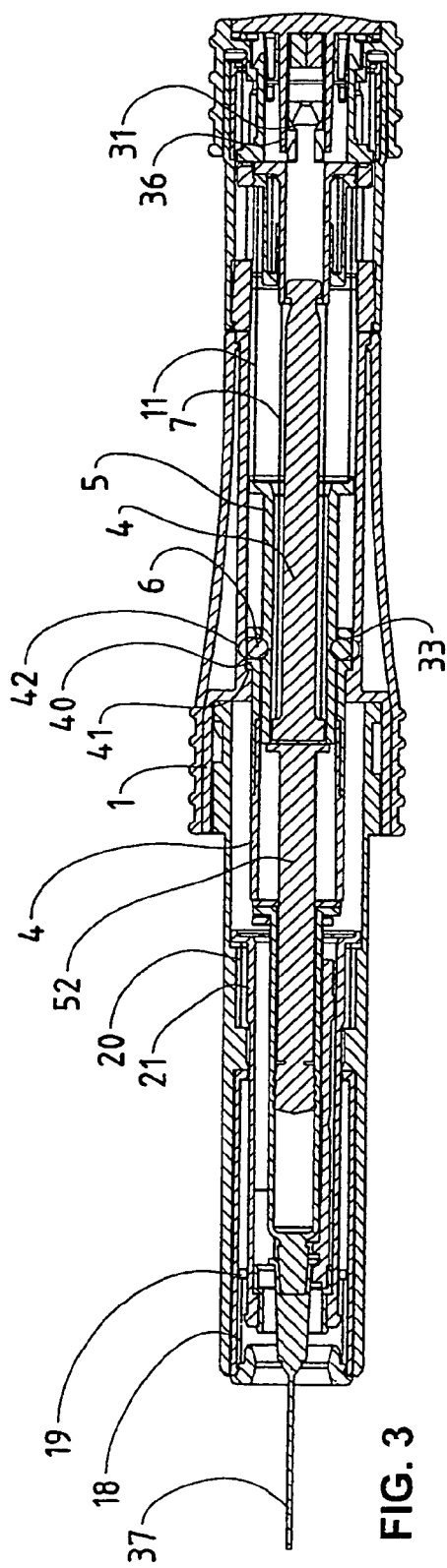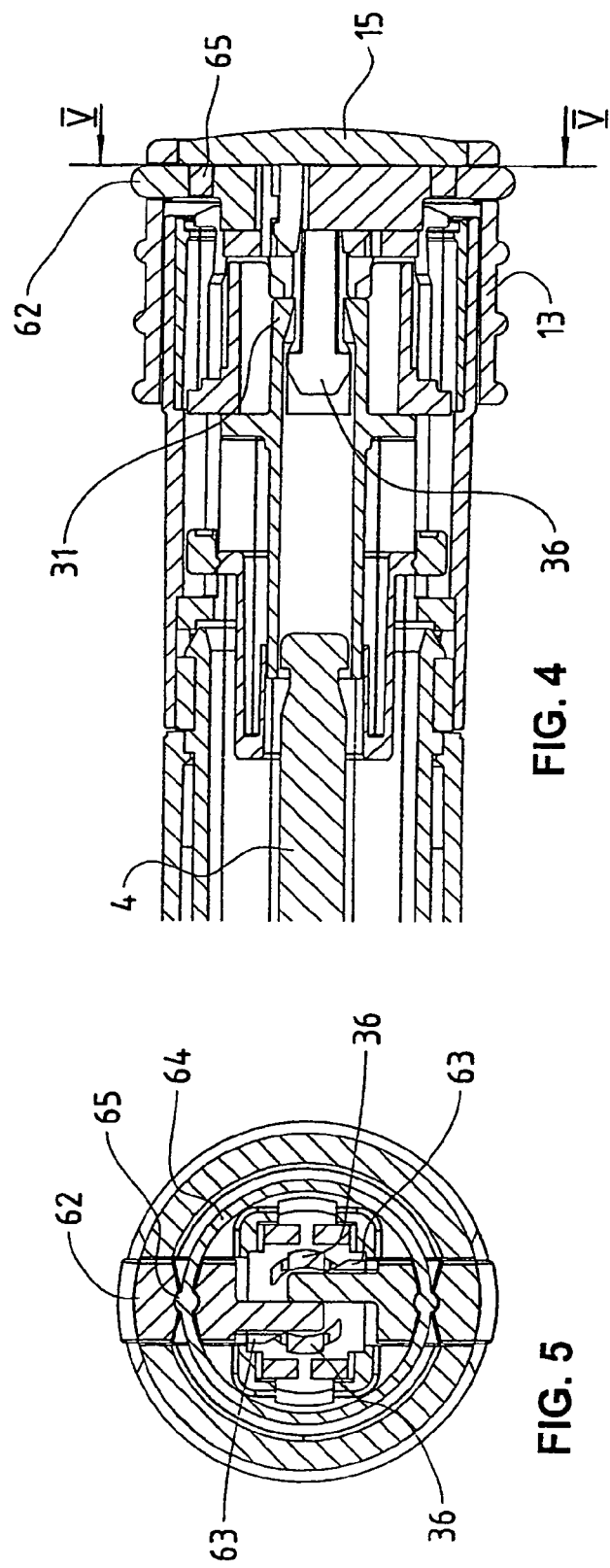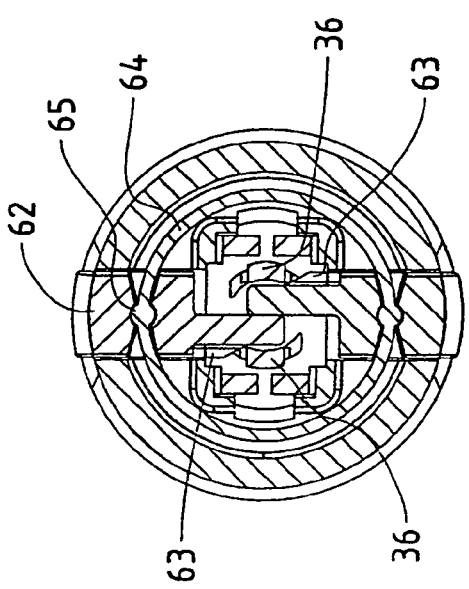

AUTO-INJECTOR COMPRISING A RESETTABLE RELEASING SAFETY DEVICE

CROSS-REFERENCE TO RELATED APPLICATIONS

This application is a continuation of International Patent Application No. PCT/CH2003/00758, filed on Nov. 17, 2003, which claims priority to Swiss Application No. 1987/02, filed on Nov. 25, 2002, the contents of which are hereby incorporated by reference in their entirety.

BACKGROUND

The present invention relates to devices and methods of dispensing, administering, injecting or delivering substances. More particularly, it relates to devices and methods for making injections, including autoinjectors for the automatic injection of an active substance, such as medicinal substances, insulin, etc.

Typically, such autoinjectors have a receptacle for the active substance, which receptacle, together with a connected injection needle, is displaceable within a housing by spring force for the purpose of inserting the injection needle. Such autoinjectors typically have a syringe piston, which, for the purpose of expelling the active substance, is displaceable within the receptacle through spring force, transfer means that transfer the spring force to the receptacle and/or to the syringe piston, holding means for holding the transfer means, and releasing means for causing the holding means to release the transfer means when the releasing means are brought from a first position into a second position.

Autoinjectors of the type mentioned above are known in many embodiments. One use they serve is for the self-administration of medication by a patient. Many of the known autoinjectors include a releasing safety device, which is intended to prevent an injection procedure from being inadvertently triggered. These releasing safety devices are, in most cases, components that block the releasing means from being activated. These components may be, for example, formed as slides that are movable in relation to the releasing means or as covers or stoppers that are to be removed prior to the injection. These additional components obviously increase the production costs of autoinjectors, as well as complicate their use.

SUMMARY

Objects of the present invention include to provide an autoinjector in which the releasing means does not require additional operating elements, and to provide an autoinjector that can be unlocked and locked again without triggering an injection.

According to the present invention, this is achieved by providing an actuable resetting means which make it possible to bring a releasing means from a first position into a second position without, in the process, causing a transfer means to become unblocked.

In one embodiment of the present invention, the unlocking takes place through the bringing of the releasing means from the second position into the first position. Starting from this first position, an injection can now be triggered through the bringing of the releasing means into the second position. On the other hand, however, through actuation of the resetting means, the releasing means can be brought again from the first position back into the second position without the triggering of an injection. An autoinjector according to the present invention has relatively few components and is simple and reliable in its operation.

In one embodiment, the present invention comprises an autoinjector comprising a housing, a receptacle for an active substance, which receptacle, together with a connected injection needle, is displaceable within the housing by spring force for inserting the injection needle into a patient, a piston displaceable within the receptacle by spring force for expelling the active substance, a transfer mechanism for transferring the spring force to the receptacle and/or to the piston, a holding mechanism for holding the transfer mechanism, a releasing mechanism for causing the holding mechanism to release the transfer mechanism when the releasing mechanism is moved from a first position into a second position, and a resetting mechanism for moving the releasing mechanism from the first position into the second position without during the move causing the transfer mechanism to be released.

In one embodiment, the present invention comprises an injection device comprising a syringe which can be displaced within a housing by means of the power exercised by springs. Transducing means transduce said spring power to the syringe while resilient stopping cams which engage into a groove of the transducing means maintain the transducing means in the initial position thereof until being released. In order to prepare an injection, an axially displaced releasing head is pulled back from a first position into a second position in which the safety device of the autoinjector is released. In order to trigger an injection, the releasing head is moved forward, resilient tongues that are disposed on the releasing head engaging with the stopping cams so as to push said stopping cams apart. Resetting buttons which are disposed inside the releasing head act upon the resilient tongues when being pressed such that the resilient tongues do not engage with the stopping cams when the releasing head is moved forward.

In one embodiment of an autoinjector in accordance with the present invention, holding means are designed as elastic nubs that engage with their free ends a recess that is provided on a transfer means. Releasing means comprise elastic tongues that act on the elastic nubs and bring the latter out of their engagement in the recess, when the releasing means are moved from a first into a second position. These measures make possible a simple design, and the elastic nubs and the elastic tongues can be produced as plastic parts in the injection-molding process. It thereby becomes possible, according to a further embodiment of the invention, to so design the resetting means that through their actuation the elastic tongues become elastically deformed in such a way that the tongues do not act on the elastic nubs when the releasing means are brought from the first into the second position.

According to one preferred embodiment of the present invention, the releasing means display a releasing head that is axially displaceable in relation to the housing. This makes possible operation of an autoinjector using only one hand. If the releasing head in its first position is further back than in its second position, then it can be pushed forward for the releasing, which promotes the correct positioning of the autoinjector on the skin of the patient. If, in addition, the releasing head is arranged at the rear end of the housing, i.e., the end opposite to the injection needle, then the actuation of the releasing head is further facilitated, because in order to trigger the injection the user can then either take hold of the periphery of the actuation head or press on its rear face.

Spring means that prestress the releasing head in the direction of its second position are provided according to a further embodiment of the invention. This promotes not only the releasing or the resetting into the locked position, but also ensures that the releasing means remains in the second position after the injection. Advantageously, the resetting means display at least one push-button that is accommodated in the releasing head and is actuable in a direction generally radial to the longitudinal axis of the autoinjector. Thus, with a depressed push-button the releasing head can be guided from the first into the second, locked position.

BRIEF DESCRIPTION OF THE DRAWINGS

FIG. 1 is a longitudinal section through an embodiment of an autoinjector according to the present invention, in a loaded state;

FIG. 2 is a longitudinal section through the autoinjector of FIG. 1 in an unlocked state, the sectional plane being rotated 90° in relation to FIG. 1;

FIG. 3 is a longitudinal section through the autoinjector of FIG. 1 after the insertion of the injection needle, the section being made through the same plane as in FIG. 2;

FIG. 4 is a longitudinal section through the rear part of the autoinjector in the same operating position as in FIG. 3, the section being made through the same plane as in FIG. 1; and FIG. 5 is a cross section along the line V—V of FIG. 4, in enlarged scale in relation to FIG. 4.

DETAILED DESCRIPTION OF THE DRAWINGS

An autoinjector in accordance with the present invention comprises of two main components, namely the reservoir part, shown on the left in FIGS. 1 through 3, in which a filled syringe 50 is accommodated, and the power pack, shown on the right in the same drawings, in which are situated the parts serving the insertion and expelling of the syringe 50. The two main components are detachably connected to each other through a bayonet-type connection between a receiving sleeve 16 and a power sleeve 1. In the following description, the end of the autoinjector at which the injection needle is located is referred to as the front.

With reference to FIG. 1, which shows the operationally-ready autoinjector, the power pack will be described first. The parts for the driving of the autoinjector are accommodated in the grip sleeve 14, to the rear end of which is attached an indicator window 51. The indicator window 51 is produced of transparent or translucent material or has openings, for example in the form of slots, which allow the observation from the outside of the indicator 12 that is displaceably accommodated in the indicator window 51. The indicator 12 is preferably formed in a ring-shaped manner and is thereby visible from any direction around the autoinjector. Arranged at the rear end of the autoinjector is the actuation head 13, which on its rear face is provided with a cover disc 15. Housed within the grip sleeve 14 is the power sleeve 1. At its rear end, the power sleeve 1 is connected to a catch sleeve 8 by means of a snap connection. The catch sleeve 8 displaceably accommodates in its interior a spring sleeve 10. The spring sleeve 10 is coupled at the rear to the indicator 12 by means of a snap connection. At the front side of the spring sleeve 10, the transfer part 5 is displaceably supported in the power sleeve 1. The transfer part 5 has the task of actuating the piston 52 of the syringe 50, in order to expel the contents of the syringe, as will be described in greater detail later. Accommodated inside the spring sleeve 10 is a spring 9 in the stressed state, which spring is supported in the front on the spring sleeve 10 and in the rear presses against the catch sleeve 8. A second spring 11, likewise in the stressed state, is located on the outside of the spring sleeve 10 and is supported in the front on the transfer part 5 and in the rear presses against the spring sleeve 10.

A piston guide 4 rests with its front, sleeve-shaped end against the shoulder of the syringe and extends through the transfer part 5, the spring sleeve 10, and the catch sleeve 8 into the region of the actuation head 13. The piston guide 4 is prestressed forward by a spring 7, which at the rear, rests on the catch sleeve 8. At its rear end the piston guide 4 is held in the position shown in FIG. 1 by means of two stopping nubs 31 formed on the catch sleeve 8, which nubs engage a groove 32 formed at the rear end of the piston guide 4. Catch members, for example balls 6, which are taken up in radial openings 33 of the piston guide 4 and engage recesses 34 in the transfer part 5, ensure in this operating position that the transfer part 5 and the piston guide 4 can only move in common. Of course, the catch members could have any suitable shape, for example that of pins.

A description of the reservoir part now follows. The parts for the accommodation of the syringe 50 are, as mentioned, housed in the receiving sleeve 16, which, as described, can be connected to the power sleeve 1. A sliding sleeve 21 accommodates within itself the syringe, with the interposition of a needle holder 22. In the case of luer slip connections, the needle holder 22 ensures that the injection needle 37 cannot be removed from the syringe so long as the latter is situated in the autoinjector. At the front, the needle holder 22 lies against a support ring 24 connected to the sliding sleeve 21. In the case of syringes and needle having luer lock couplings, in which therefore the injection needle is connected to the syringe by means of a thread, no needle holder 22 is present. The sliding sleeve 21 is displaceable within the receiving sleeve 16 and is pushed by a spring 20 into the operating position shown in FIG. 1. A sleeve-shaped needle protector 17 is displaceable within the receiving sleeve 16. The needle protector 17 is closed at the front by a snap cover 23, which leaves open a passage for the injection needle, and at its rear end has an inward-pointing flange 35. A spring 18 rests at the front against the snap cover 23 and at the rear against a carrier ring 19. In this figure, the spring 18 is in its relaxed state.

In preparation for the injection, the autoinjector must be brought from the locked state shown in FIG. 1 into the unlocked state, as represented in FIG. 2. For this purpose, the actuation head 13 is moved rearward. This can take place in that the apparatus is grasped with one hand on the receiving sleeve 16 and with the other hand on the actuation head 13, and the two parts are pulled apart. However, by virtue of the design and arrangement of the actuation head 13, it is also possible to hold on to the auto injector at the grip sleeve 14 and, with the thumb of the same hand, to push the actuation head 13 rearward. Circumferential ribs provided on the actuation head 13 can prevent a slipping of the thumb. This rearward pushing of the actuation head 13 is referred to as the unlocking movement in the following. In the unlocking movement, a region of the indicator window 51 at the front edge of the actuation knob 13 is opened, on the inside of which window a conspicuously-colored (e.g., red) warning sleeve 53 becomes visible, which indicates clearly that the autoinjector is now unlocked and ready for the injection. During the unlocking movement, tongues 36, which are formed at the inside on the cover disc 15 of the actuation head 13, are displaced by the stopping nubs 31 formed on the catch sleeve. The tongues and the stopping nubs are shaped such that in the unlocking movement the tongues 36 give way radially in an elastic manner while they slide over the ends of the stopping nubs 31, which hold on to the piston guide 4 by engaging the mentioned groove 32. After the unlocking movement, the tongues 36 formed on the actuation head 13 act as wedges between the stopping nubs 31. The shape of the tongues 36 can be seen especially clearly in FIG. 4. The unlocking movement causes the stressing of a spring 3, which acts between hooks formed on the catch sleeve 8 and a retaining part 60 fastened in the actuating head by a snap connection, thus pushing the actuation head into its initial position according to FIG. 1 and thus ensuring that the tongues 36 rest against the stopping nubs 31 with a slight prestress. The autoinjector is now ready for the injection and is positioned with the snap cover 23 at the desired location on the skin of the patient. The patient holds on to the autoinjector at the grip sleeve 14. To trigger the injection, only a pushing forward of the actuation head 13, i.e., in the direction of the body of the patient, must now be carried out.

In the triggering movement, the tongues 36 press between the stopping nubs 31 and spread these radially apart, whereby the piston guide 4 is released and thrust forward by the force of the spring 7. The insertion is also supported by the force of the springs 9 and 1 1, which act on the transfer part 5. Since the transfer part 5 is connected to the piston guide 4 via the balls 6, there exists a spring system, consisting of the springs 7, 9, and 11, having a relatively high initial force, which contributes to the reliable pushing forward of the injection needle to the full penetration depth. The force of the springs is transferred via the slotted, sleeve-shaped front end 4' of the piston guide 4 to the shoulder of the syringe 50 and pushes the syringe forward, together with the sliding sleeve 21 in which the syringe is accommodated, so that the injection needle 37 is pushed forward and penetrates the skin of the patient. In this movement, the sliding sleeve 21 compresses both the spring 20 and—via the carrier ring 19—the spring 18. The insertion stroke is limited by the abutting of the shoulder 40 of the piston guide 4 against an inner step 41 of the power sleeve 1. In this end position, the openings 33 in the piston guide 4, which openings accept the balls 6, are aligned with recesses 42 provided in the power sleeve 1, the balls 6 can give way to the outside, and the coupling between the piston guide 4 and the transfer part 5 is abolished. Simultaneously, the piston guide 4 is now locked against the power sleeve 1, so that the force of the spring 20 is taken up by the power sleeve and consequently does not act against the force of the spring 7. Thus, the injection can now automatically begin, in that the piston 52 of the syringe is thrust forward further by the transfer part 5 under the force of the springs 11 and 9. Simultaneously with the insertion motion, the spring 18 is stressed by the carrier ring 19, which is moved by the sliding sleeve 21 in a leftward direction in the drawings.

FIG. 3 shows the autoinjector in the operating state just described. The needle 37 is fully extended, while the medication is still located in the syringe 50. Starting from the operating state shown in FIG. 3, the expelling of the medication now takes place automatically. The balls 6 release the transfer means 5 in such a way that the transfer means can move into the piston guide 4 and in the process can actuate the piston 52 of the syringe. Through the gradual relaxing of the springs 11 and 9, the spring sleeve 10, and with it the indicator 12, is shifted forward, so that the indicator 12 reaches its end position when the piston 52 is all the way forward in the syringe 50 and, consequently, all of the liquid present in the syringe has been expelled. As a result, the user is able to follow the course of the injection process and sees, with the aid of the indicator 12, that the entire contents of the syringe has been expelled. The distance that the indicator 12 covers is independent of the stroke of the piston 52 of the syringe and can be substantially shorter than the stroke of the transfer part 5. Through this means, on the one hand an unnecessary long autoinjector is avoided, and on the other hand, syringes with different strokes can be used with the same autoinjector. This structure also has the additional advantage that the relatively high initial force of the springs 9 and 11 is used for the insertion process and, subsequently, the relatively low ending force is utilized for the injection process, which therefore takes place more slowly, as is desirable.

Elastic tongues 38 provided in the sliding sleeve 21 are, at the beginning of the insertion stroke, prevented from protruding outward by a circumferential, inward-projecting step 39 of the receiving sleeve 16. At the end of the insertion stroke, the elastic tongues protrude beyond the jacket surface of the sliding sleeve 21. After the indicator 12 has signaled the complete expelling of the medication, the user can withdraw the autoinjector. The spring 18, which had been prestressed during the insertion process, ensures that the needle protector 17 remains in contact with the skin of the patient during the withdrawal of the autoinjector. Thus, the needle protector 17 shifts forward in relation to the receiving sleeve 16 until it completely covers the injection needle 37. The elastic tongues 38 snap outward behind the flange 35 of the needle protector 17 and ensure that the latter cannot be pushed back into the receiving sleeve 16. Any risk of an unintentional injury by the injection needle is thereby substantially eliminated.

The situation may arise in which a user does not wish to carry out an injection after having unlocked the autoinjector, whether it be because he flinches from doing it or because he is disturbed. It would be very dangerous to simply lay aside the autoinjector in the unlocked state. Thus, in the autoinjector according to the invention means are provided that allow the unlocked autoinjector to be brought back again into the locked state without triggering the injection. These means include resetting buttons 62 having a tapered region 63, which buttons project radially through the releasing head 13 from opposite sides and extend between the tongues 36, as can be seen clearly in FIG. 5. If these resetting buttons 62 are pressed, their wedge-shaped regions 63 move between the tongues 36 and spread these apart. Now the releasing head 13 can be pushed back again from the position shown in FIG. 2 into the position shown in FIG. 1, without a triggering of an injection taking place. This resetting movement, in which the spread tongues slide over the stopping nubs 31 without pressing the latter, is supported by the force of the spring 3. The resetting buttons are guided in the releasing head 13 in a radially-sliding manner. An elastic ring 64, which reaches with pins 65 into corresponding bores in the resetting buttons 62, holds the resetting buttons 62 in position, as is especially clear in FIG. 5. Simultaneously, this elastic ring 64 serves as a restoring spring in order to restore the resetting buttons 62 to their initial position after the pressing, as is shown in FIG. 5. Upon actuation of the resetting buttons 62 the elastic ring 64 is deformed from the shown circular shape into an elliptical shape. In principle, the task of the resetting could also be achieved by a single restoring resetting button, which is this case would be symmetrically tapered, so that upon actuation it would be pushed between the tongues 36 in the manner of a wedge. However, in some embodiments, two resetting buttons 62 are ergonomically preferable, since these can be compressed, for example, with the thumb and index finger, whereupon the releasing head 13 reverts to the locked position through the force of the spring 3.

While various embodiments, including preferred embodiments, of the present invention have been described herein, it is contemplated that various modifications could be made without deviating from the spirit of the present invention. Accordingly, it is intended that the scope of the present invention be dictated by the appended claims.

The invention claimed is:

1. An autoinjector comprising:
   a housing;
   a receptacle for an active substance, which receptacle, together with a connected injection needle, is displaceable within the housing by spring force for inserting the injection needle into a patient;
   a piston displaceable within the receptacle in a dose delivery direction by spring force for expelling the active substance;
   a transfer mechanism for transferring the spring force to at least one of the receptacle and piston;
   a holding mechanism for holding the transfer mechanism;
   a releasing mechanism for releasing the holding mechanism, wherein the releasing mechanism is enabled by moving the releasing mechanism in a direction substantially opposite to the dose delivery direction from a first position into a second position, and wherein the releasing mechanism releases the holding mechanism when it is moved in the dose delivery direction from the second position to the first position, thereby releasing the transfer mechanism; and
   a resetting mechanism for disengaging the releasing mechanism when the releasing mechanism is in the second position prior to delivery of the dose to enable the releasing mechanism to be moved in the dose delivery direction to the first position without releasing the holding mechanism.

2. An autoinjector for the automatic injection of an active substance, said autoinjector comprising a receptacle for the active substance, which receptacle, together with a connected injection needle, is displaceable within a housing by spring force for the purpose of inserting the injection needle, a syringe piston, which for the purpose of expelling the active substance is displaceable within the receptacle by spring force, a transfer means that transfer the spring force to at least one of the receptacle and syringe piston in an injection delivery direction, a holding means for holding the transfer means, a releasing means for releasing the holding mechanism, wherein the releasing means is enabled by moving the releasing means in a direction substantially opposite to the injection delivery direction from a first position into a second position, and wherein the releasing means releases the holding means when it is moved in the injection delivery direction from the second position to the first position, thereby releasing the transfer means, and selectively actuable resetting means for disengaging the releasing means when the release means is in the second position prior to delivery of the injection to enable the releasing means to be moved in the injection delivery direction to the first position without releasing the holding means.

3. The autoinjector according to claim 2, wherein the holding means comprises elastic nubs that with their free ends engage a recess provided on the transfer means.

4. The autoinjector according to claim 3, wherein the releasing means comprises elastic tongues that act on the elastic nubs and bring the nubs out of engagement in the recess when the releasing means are moved from the second into the first position.

5. The autoinjector according to claim 4, wherein actuating the resetting means causes the elastic tongues to elastically deform so the tongues do not act on the elastic nubs when the releasing means are brought the second into the first position.

6. The autoinjector according to claim 5, wherein the releasing means comprise a releasing head axially displaceable in relation to the housing.

7. The autoinjector according to claim 2, further comprising spring means for urging the releasing means in the direction of its first position from its second position.

8. The autoinjector according to claim 7, wherein the resetting means comprises at least one pushbutton accommodated in the releasing means and actuable generally radially with respect to a longitudinal axis of the autoinjector.

9. An autoinjector, comprising:
   a housing for enclosing a reservoir, an injection needle fluidly coupled to the reservoir, and a piston for displacing fluid in the reservoir though the injection needle to deliver a dose to a patient;
   a transfer mechanism for applying a transferring force to the piston in a dose delivery direction, wherein the transfer mechanism is spring-loaded;
   a gripping mechanism that grips the transfer mechanism to prevent movement of the transfer mechanism prior to applying the transferring force to the piston;
   a trigger mechanism for triggering operation of the transfer mechanism, thereby delivering the dose to the patient;
   a release mechanism coupled to the trigger mechanism, wherein the release mechanism is enabled by moving the trigger mechanism in a direction substantially opposite to the dose delivery direction from a first position into a second position, and wherein the release mechanism releases the gripping mechanism when the trigger mechanism is moved from the second position to the first position, thereby delivering the dose to the patient; and
   a resetting mechanism coupled to the trigger mechanism for disengaging the release mechanism when the trigger mechanism is in the second position prior to delivery of the dose to enable the trigger mechanism to return to the first position without releasing the gripping mechanism.

10. The autoinjector of claim 9, wherein the gripping mechanism comprises elastic nubs that engage grooves in the transfer mechanism.

11. The autoinjector of claim 10, wherein the release mechanism comprises a wedge-shaped elastic tongue that releases the elastic nubs of the gripping mechanism by sliding between the nubs to disengage the nubs from the grooves in the transfer mechanism when the trigger mechanism is moved from the second position to the first position, thereby enabling the transfer mechanism to apply spring-loaded force to the piston.

12. The autoinjector of claim 11, wherein the resetting mechanism comprises a tab that separates the wedge-shaped elastic tongue from the nubs to enable the wedge-shaped elastic tongue to slide past the nubs without disengaging the nubs from the grooves of the transfer mechanism when the trigger mechanism is moved from the second position to the first position.

* * * * *